US008406877B2

(12) United States Patent
Smith et al.

(10) Patent No.: US 8,406,877 B2
(45) Date of Patent: Mar. 26, 2013

(54) SELECTIVE NERVE STIMULATION WITH OPTIONALLY CLOSED-LOOP CAPABILITIES (75) Inventors: David J. Smith, Shoreview, MN (US); Randy Westlund, River Falls, WI (US); Imad Libbus, St. Paul, MN (US)

(73) Assignee: Cardiac Pacemakers, Inc., St. Paul, MN (US)

( * ) Notice: Subject to any disclaimer, the term of this patent is extended or adjusted under 35 U.S.C. 154(b) by 1194 days.

(21) Appl. No.: 11/687,809

(22) Filed: Mar. 19, 2007

(65) Prior Publication Data
US 2008/0234780 A1 Sep. 25, 2008

(51) Int. Cl.
*A61N 1/00* (2006.01)
(52) U.S. Cl. ........... 607/17; 607/116; 607/117; 607/118
(58) Field of Classification Search ................ 607/17, 607/116–118
See application file for complete search history.

(56) References Cited

U.S. PATENT DOCUMENTS

| | | | | |
|---|---|---|---|---|
| 5,014,698 A | * | 5/1991 | Cohen | 607/4 |
| 5,330,507 A | * | 7/1994 | Schwartz | 607/14 |
| 5,690,681 A | | 11/1997 | Geddes et al. | |
| 6,052,624 A | | 4/2000 | Mann | |
| 6,205,361 B1 | | 3/2001 | Kuzma et al. | |
| 6,393,325 B1 | * | 5/2002 | Mann et al. | 607/46 |
| 6,473,644 B1 | | 10/2002 | Terry, Jr. et al. | |
| 6,600,954 B2 | | 7/2003 | Cohen et al. | |
| RE38,705 E | * | 2/2005 | Hill et al. | 607/9 |
| 6,907,293 B2 | | 6/2005 | Grill et al. | |
| 7,020,530 B1 | | 3/2006 | Ideker et al. | |
| 7,072,720 B2 | | 7/2006 | Puskas | |
| 7,162,304 B1 | | 1/2007 | Bradley | |
| 7,363,086 B1 | * | 4/2008 | Koh et al. | 607/42 |
| 2003/0045909 A1 | | 3/2003 | Gross et al. | |
| 2003/0055461 A1 | * | 3/2003 | Girouard et al. | 607/17 |
| 2003/0055476 A1 | | 3/2003 | Vinup et al. | |
| 2004/0093053 A1 | | 5/2004 | Gerber et al. | |
| 2005/0004639 A1 | | 1/2005 | Erickson | |
| 2005/0060009 A1 | | 3/2005 | Goetz | |

(Continued)

FOREIGN PATENT DOCUMENTS
WO  WO-2006/121929 A1  11/2006
WO  WO2006127366 A1  11/2006
(Continued)

OTHER PUBLICATIONS

Libbus, Imad, et al., "System and Method for Closed-Loop Neural Stimulation", U.S. Appl. No. 11/279,188, filed Apr. 10, 2006, 58 Pages.

(Continued)

*Primary Examiner* — Nicole F Lavert
(74) *Attorney, Agent, or Firm* — Faegre Baker Daniels LLP (57) ABSTRACT

Systems and methods for steering one or more stimulation fields to a selected nerve target, thereby optimizing one or a combination of low stimulation thresholds, desired therapy outcomes, or a minimization of adverse stimulation side-effects. An array of electrodes disposed, at least in part, on two or more neural stimulation leads are used for steering the stimulation fields to the selected nerve target and are positioned adjacent the selected target. The stimulation may be titrated based on, among other things, a detected physiologic response to the applied stimulation.

28 Claims, 7 Drawing Sheets

U.S. PATENT DOCUMENTS

| | | | |
|---|---|---|---|
| 2005/0137668 A1* | 6/2005 | Khan | 607/118 |
| 2005/0143786 A1* | 6/2005 | Boveja | 607/45 |
| 2005/0149154 A1* | 7/2005 | Cohen et al. | 607/118 |
| 2005/0165457 A1* | 7/2005 | Benser et al. | 607/42 |
| 2005/0187589 A1 | 8/2005 | Wallace et al. | |
| 2005/0197675 A1* | 9/2005 | David et al. | 607/9 |
| 2006/0030919 A1 | 2/2006 | Mrva et al. | |
| 2006/0116737 A1 | 6/2006 | Libbus | |
| 2006/0161235 A1 | 7/2006 | King | |
| 2006/0206159 A1 | 9/2006 | Moffitt et al. | |
| 2006/0259107 A1 | 11/2006 | Caparso et al. | |
| 2006/0271118 A1 | 11/2006 | Libbus et al. | |
| 2007/0066998 A1 | 3/2007 | Hansen et al. | |
| 2007/0142864 A1 | 6/2007 | Libbus et al. | |
| 2008/0051839 A1* | 2/2008 | Libbus et al. | 607/2 |

FOREIGN PATENT DOCUMENTS

| | | | |
|---|---|---|---|
| WO | WO-2008115507 A1 | 9/2008 | |

OTHER PUBLICATIONS

Libbus, Imad, et al., "System for Abating Neural Stimulation Side Effects", U.S. Appl. No. 11/467,264, filed Aug. 25, 2006, 53 Pages.

Libbus, Imad, et al., "System for Neurally-Mediated Anti-Arrhythmic Therapy", U.S. Appl. No. 11/538,488, filed Oct. 4, 2006, 37 Pages.

McCabe, Aaron, et al., "Closed Loop Neural Stimulation Synchronized to Cardiac Cycles", U.S. Appl. No. 11/459,481, filed Jul. 24, 2006, 59 Pages.

"International Application Serial No. PCT/US2008/003574, International Search Report mailed Jul. 25, 2008", 5 pgs.

"International Application Serial No. PCT/US2008/003574, Written Opinion mailed Jul. 25, 2008", 8 pgs.

* cited by examiner

SELECTIVE NERVE STIMULATION WITH OPTIONALLY CLOSED-LOOP CAPABILITIES

TECHNICAL FIELD

This patent document pertains generally to neural stimulation systems and methods. More particularly, but not by way of limitation, this patent document pertains to systems and methods for selective nerve stimulation with optionally closed-loop capabilities.

BACKGROUND

The nervous system serves as the body's control center and electrical-chemical communications network. The nervous system processes countless bits of information and generates appropriate reactions by sending electro-chemical impulses through nerves to the body's effector organs, such as the muscles and glands. The nervous system is comprised of the central nervous system (CNS), which includes the brain and spinal cord, and the peripheral nervous system (PNS), which connects nerve processes to effectors and receptors.

The PNS has two parts: the somatic nervous system (SNS) and the autonomic nervous system (ANS). The SNS, or voluntary nervous system, enables humans to react consciously to environmental changes. This system controls movements of "voluntary" muscles. The ANS, on the other hand, regulates "involuntary" organs and maintains normal internal function. The efferent portion of the ANS is divided into sympathetic and parasympathetic systems. The sympathetic nervous system is affiliated with stress and the "fight or flight response" to emergencies, while the parasympathetic nervous system is affiliated with relaxation and the "rest and digest response."

Autonomic balance reflects the relationship between parasympathetic and sympathetic activity and may provide an indication of a body's well-being or lack thereof. Changes in autonomic balance are reflected in changes in heart rate, heart rhythm, contractility, remodeling, inflammation and blood pressure. Changes in autonomic balance can also be seen in other physiological changes, such as changes in abdominal pain, appetite, stamina, emotions, personality, muscle tone, sleep, and allergies, for example.

The use of nerve stimulation for treating and controlling a variety of medical, psychiatric, and neurological disorders has seen significant growth over the last several decades, including for treatment of heart conditions, epilepsy, obesity, and breathing disorders, among others. For instance, modulation of the autonomic balance with neural stimulation has been shown to be possible and have positive clinical benefits, such as protecting the myocardium from further remodeling and predisposition to fatal arrhythmias following a myocardial infarction (MI). However, stimulation of the nervous system, such as the ANS, can have unintended consequences (i.e., side-effects), including altering one's voice, coughing, pharyngitis, paresthesia, dyspnea, nausea or laryngismus, and may require considerable amounts of artificially-generated energy.

What is needed is a system and method for stimulating a selected nerve target within a nerve trunk in a way that maximizes, or nearly maximizes, the efficacy of a therapeutic stimulation signal when treating a particular disorder. What is further needed is a stimulation system and method having the ability to monitor undesirable stimulation side-effects and minimize or abate the same by changing the stimulation electrode vector combination or stimulation signal parameters used.

SUMMARY

A system for stimulating a peripheral nerve target includes an array of electrodes disposed, at least in part, on two or more neural stimulation leads positioned adjacent the peripheral nerve target, one or more physiologic sensors, and an implantable medical device. The one or more physiologic sensors are adapted to generate a signal indicative of a status of one or more physiologic parameters. The physiologic parameter indicative signal is used, at least in part, to generate a programming signal receivable by a programmable memory of the implantable medical device for selectively applying electrical stimulation to at least two electrodes within the electrode array.

Certain embodiments of the present system include an external programmer, one or more lead positioning members, or a therapy titration/adjustment circuit. The external programmer is adapted to receive and communicate one or more remotely generated inputs to the implantable medical device via a telemetry link. The one or more lead positioning members are adapted to connect and maintain a desired geometric relationship between portions of the two or more neural stimulation leads and may include an electrode thereon. The therapy titration/adjustment circuit is adapted to change one or more parameters of the applied electrical stimulation.

A method of modulating autonomic balance by stimulating a nerve target includes disposing a portion of two or more neural stimulation leads carrying an array of electrodes adjacent the nerve target, selectively employing at least two of the electrodes within the array to direct electrical stimulation applied to the electrodes to the nerve target, and delivering electrical stimulation to the selectively employed electrodes.

Certain embodiments of the present methods include evaluating a plurality of electrode vector combinations, detecting a physiologic response to the electrical stimulation, or titrating the electrical stimulation using the detected physiologic response. Some methods further include maintaining a desired geometric relationship between the two or more neural stimulation leads.

Advantageously, the present systems and methods allow for selective nerve stimulation within a nerve trunk using, among other things, a stimulation electrode vector combination chosen from multiple electrode vector combination options. In this way, the efficacy of a stimulation signal may be maximized, or nearly maximized, when treating a particular disorder. Through the multiplicity of stimulation electrode vector combination options, the systems and methods can adapt to changes in electrode/nerve tissue interface to minimize stimulation thresholds and thereby increase battery life of an implanted stimulation generating device, and can further change the electrode vector combination used to deliver the stimulation to minimize or abate undesirable stimulation side-effects. In addition, the stimulation systems and methods allow for the monitoring of a stimulation response of one or more physiologic parameters, which can in turn be used to titrate parameters of the stimulation signal or change the stimulation electrode vector combination used. These and other examples, advantages, and features of the present systems and methods will be set forth in part in the detailed description, which follows, and in part will become apparent to those skilled in the art by reference to the following description of the present systems, methods, and drawings or by practice of the same.

BRIEF DESCRIPTION OF THE DRAWINGS

In the drawings, like numerals describe similar components throughout the several views. Like numerals having different letter suffixes represent different instances of similar components. The drawings illustrate generally, by way of example, but not by way of limitation, various embodiments discussed in the present document.

DETAILED DESCRIPTION

The following detailed description includes references to the accompanying drawings, which form a part of the detailed description. The drawings show, by way of illustration, specific embodiments in which the present systems and methods may be practiced. These embodiments, which are also referred to herein as "examples," are described in enough detail to enable those skilled in the art to practice the present systems and methods. The embodiments may be combined, other embodiments may be utilized or structural, electrical or logical changes may be made without departing from the scope of the present systems and methods. The following detailed description is, therefore, not to be taken in a limiting sense, and the scope of the present systems and methods is defined by the appended claims, along with the full scope of legal equivalents to which such claims are entitled.

In this document, the terms "a" or "an" are used to include one or more than one; the term "or" is used to refer to a nonexclusive "or" unless otherwise indicated; the phrase "stimulate a selected nerve target" or similar refers to the ability of the systems and methods to activate or stimulate single axons or small groups of axons (i.e., nerve bundles) within a common nerve trunk without stimulating other portions of such nerve; and the phrase "minimizing or abating stimulation side-effects" or similar includes terminating a sensed side-effect, reducing the intensity of the sensed side-effect, reducing the intensity of potential future side-effects, or avoiding or preventing potential future side-effects. In addition, it is to be understood that the phraseology or terminology employed herein, and not otherwise defined, is for the purpose of description only and not of limitation.

The present neural stimulation systems and methods can effectively and efficiently be used to treat and control a variety of disorders, such as medical, psychiatric, or neurological disorders, by modulation of autonomic balance. Changes in autonomic balance can be monitored by sensing changes to a status of one or more physiologic parameters (e.g., changes in heart rate or blood pressure), with therapeutic stimulation applied to a selected nerve target via an optimal or acceptable electrode vector combination in response to the sensed physiologic changes. Advantageously, by employing a plurality of electrode bearing leads (e.g., two or more), portions of which are positioned adjacent a nerve trunk of interest, a multiplicity of electrode vector combinations are available to the system for adequately stimulating one or more selected portions of the nerve trunk at low stimulation thresholds and with minimal adverse side-effects.

Figure 1:
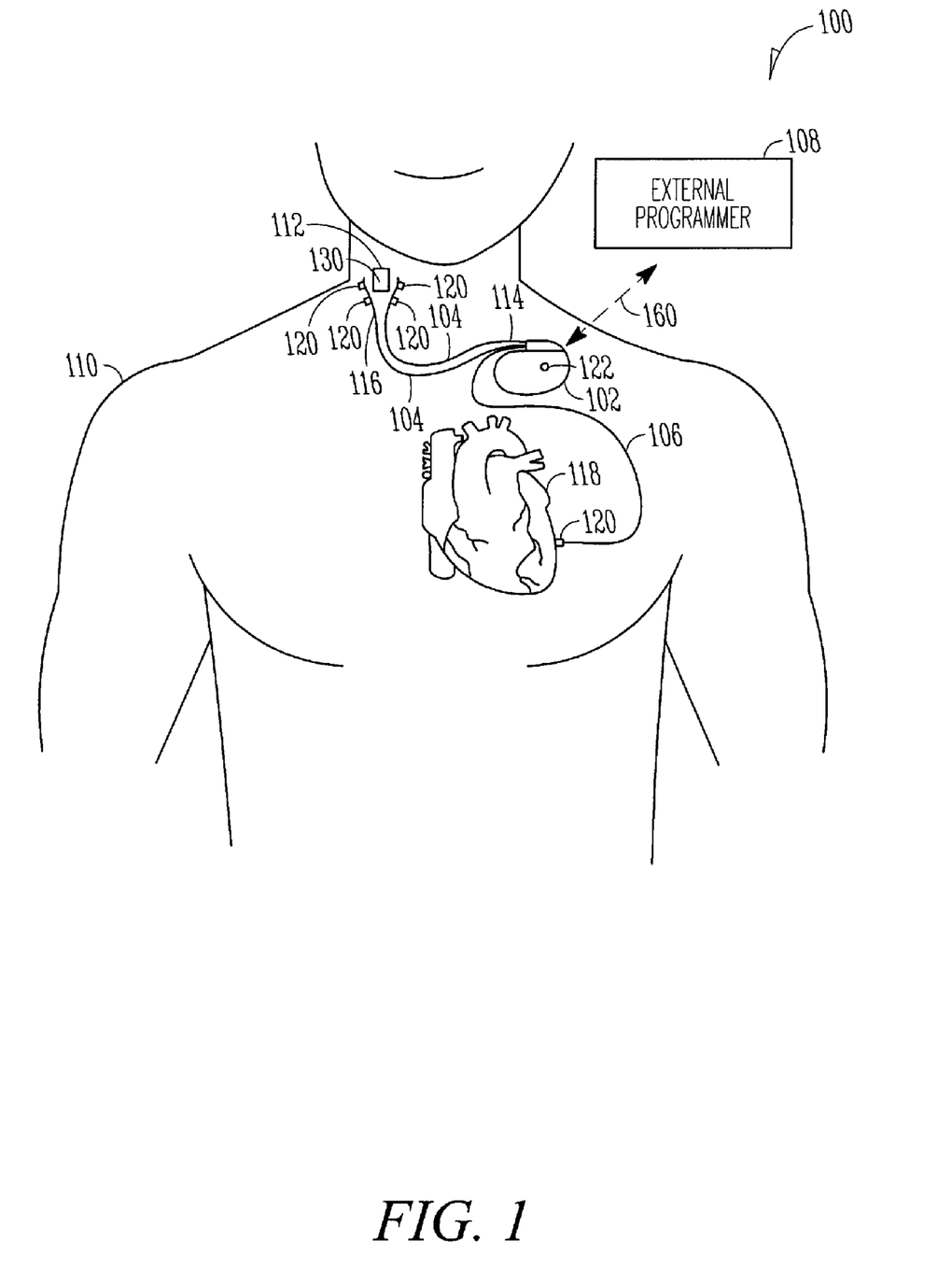
FIG. 1 illustrates a neural stimulation system including an implantable medical device, a plurality of leads, an external programmer, and an environment in which the system may be used, as constructed in accordance with at least one embodiment.

FIG. 1 illustrates a neural stimulation system 100 including an implantable medical device (IMD) 102, two or more neural stimulation leads 104, a cardiac stimulation lead 106, and an external programmer 108 communicatable with the IMD 102 via a telemetry link 160. As shown, the IMD 102 is subcutaneously or submuscularly positioned in a patient's 110 chest. The two or more neural stimulation leads 104 and the cardiac stimulation lead 106 are connected to the IMD 102 on their respective proximal ends 114. In various embodiments, the distal ends 116 of the neural stimulation leads 104 each include at least one electrode 120 and are positioned adjacent a nerve trunk 112 of interest, such as the vagus nerve, thereby electrically connecting the IMD 102 and the nerve trunk 112. A distal end 116 of the cardiac stimulation lead 106 includes at least one electrode 120 and is positioned within, on, or about a heart 118, thereby electrically connecting the IMD 102 and the heart 118.

Each electrode 120 of the neural stimulation leads 104 and the cardiac stimulation lead 106 can be programmed by the IMD 102 to assume a positive or negative polarity to create a particular stimulation field (see FIG. 3) when current, for example, is applied thereto. Thus, many different vector combinations of programmed anode and cathode electrodes can be used to deliver a variety of current density field waveforms to stimulate a selected nerve target 130 (i.e., a selected portion of the nerve trunk 112 without stimulating other portions of the nerve) or a selected heart 118 target. In addition to the lead electrodes 120, one or more leadless electrodes 122, such as an electrode associated with the IMD 102 (e.g., a "can" electrode), may be used thereby adding to the vector electrode combinations available for stimulation or sensing purposes.

Neural stimulation can be used to stimulate nerve traffic or inhibit nerve traffic. One example of neural stimulation to stimulate nerve traffic is a low frequency signal (e.g., a signal within a range of about 20 Hz to 50 Hz). One example of neural stimulation to inhibit nerve traffic is a high frequency signal (e.g., a signal within a range of about 120 Hz to 150 Hz). Other methods for stimulating and inhibiting nerve traffic include anodal block of nerve traffic.

According to various embodiments, the distal end 116 of at least one neural stimulation lead 104 is subcutaneously tunneled to a position adjacent the nerve trunk 112 of interest, and may include a nerve cuff electrode (see FIGS. 2A, 2B) to directly stimulate the selected nerve target 130 within the nerve trunk 112. The distal ends 116 of some neural stimulation lead 104 embodiments are intravascularly fed into a vessel proximal to the selected nerve target 130 (see FIGS. 2A, 2C), and use electrode(s) within the vessel to transvascularly stimulate the nerve target 130. Among other techniques, the intravascularly fed leads may be fixated with the vessel using one or more preformed bias portions of the lead body (see FIGS. 2A, 2C). As one example, some embodiments stimulate a select portion of the vagus nerve using electrode(s) positioned within the internal jugular vein. As another example, some embodiments deliver neural stimulation to the selected nerve target 130 from within the trachea, the laryngeal branches of the internal jugular vein, or the subclavian vein. Besides one or more portions of the vagus nerve, other selected nerve targets 130 may be stimulated, such as one or more portions of a baroreceptor, a cardiac nerve, or a cardiac fat pad.

As generally illustrated in FIGS. 2A-2D, electrical neural stimulation generated by the IMD 102 (FIG. 1) may be delivered to a selected nerve target 230 using, at least in part, any combination of neural stimulation cuff leads 202, neural stimulation intravascular leads 204, or neural stimulation subcutaneous leads 206. According to various embodiments, the distal end portions 216 of the neural stimulation leads 202, 204, 206 are positioned adjacent a nerve trunk 112 (FIG. 1), the selected target portion 230 of which is to be stimulated. Among other implantation techniques, the neural stimulation leads 202, 204, 206 may be positioned by surgical dissection, endoscopy, or transvascularly after access to the vasculature via subcutaneous stick or other standard means.

Figure 2A:
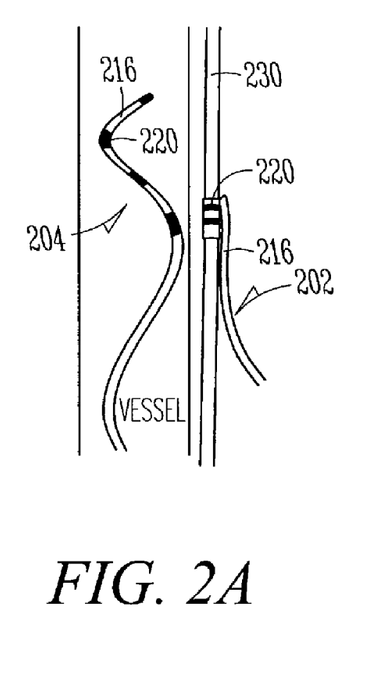
FIGS. 2A-2D illustrate a plurality of neural stimulation leads or lead positioning members, portions of which are positioned adjacent a selected nerve target, as constructed in accordance with various embodiments.
Figure 2B:
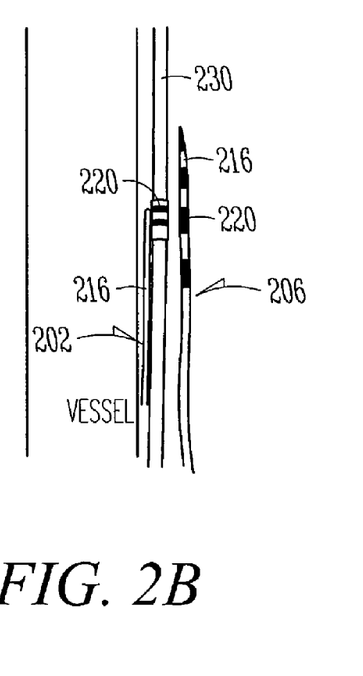
Figure 2C:
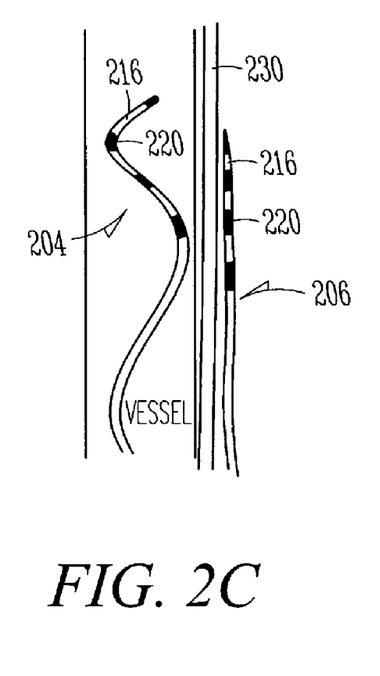
Figure 2D:
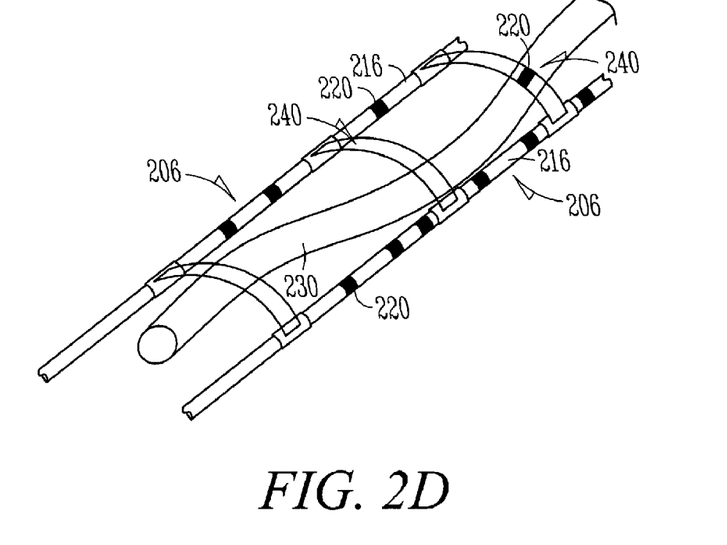

In FIG. 2A, distal ends 216 of a neural stimulation cuff lead 202 and a neural stimulation intravascular lead 204 are positioned adjacent a selected nerve target 230 within a nerve trunk. FIG. 2B illustrates distal ends 216 of a neural stimulation cuff lead 202 and a neural stimulation subcutaneous lead 206 positioned adjacent a selected nerve target 230. FIG. 2C illustrates distal ends 216 of a neural stimulation intravascular lead 204 and a neural stimulation subcutaneous lead 206 positioned adjacent a selected nerve target 230. Finally, in FIG. 2D, two neural stimulation subcutaneous leads 206 are positioned adjacent a selected nerve target 230. Each lead distal end 216 includes at least one electrode 220, such as multiple electrodes 220, forming an electrode array (including inter- and intra-lead combinations) around the selected nerve target 230. In addition, one or more lead positioning members 240 of any size, shape, or orientation may be used to connected and maintain a specific geometric relationship between the two or more lead distal ends 216. As shown in FIG. 2D, the lead positioning members 240 extend substantially perpendicular to an axis of each lead distal end 216. In one example, the lead positioning members 240 are sized and shaped to position the lead distal ends 216 adjacent the selected nerve target 230. In another example, the lead positioning members 240 include a flexible a material, such as silicone or polyurethane, and in this way may apply gentle pressure on the selected nerve target 230. In yet another example, the lead positioning members 240 may be adapted to hold an orientation between more than two leads 206. These lead positioning members 240 may further include one or more electrodes 220 thereon adding to the electrode array around the selected nerve target 230. Advantageously, the electrode array of the present subject matter provides numerous electrode vector combinations to stimulate the selected nerve target 230.

The electrode array positioned around the selected nerve target 230, and more specifically, the numerous electrode vector combinations provided by the two or more electrode bearing leads 202, 204, 206, allow for stimulation current density fields to be steered as needed or desired (between the electrodes 220) to effectively and efficiently treat a particular medical, psychiatric, or neurological disorder. The different combinations of electrodes 220 are used to change the shape of the current density field in and around the selected nerve target 230. By using appropriate stimulation parameters (determined by an IMD 102 (see FIG. 1) itself or a physician or other caregiver by way of an external programmer) and electrode 220 locations within the array, a neural stimulation system 100 (see FIG. 1) can induce action potentials in the targeted nerve 230 that result in the desired treatment effect. In addition, the stimulation current density fields may be steered between two or more electrodes 220 (i.e., an electrode vector) which result in low stimulation thresholds and a minimization of stimulation side-effects.

Figure 3:
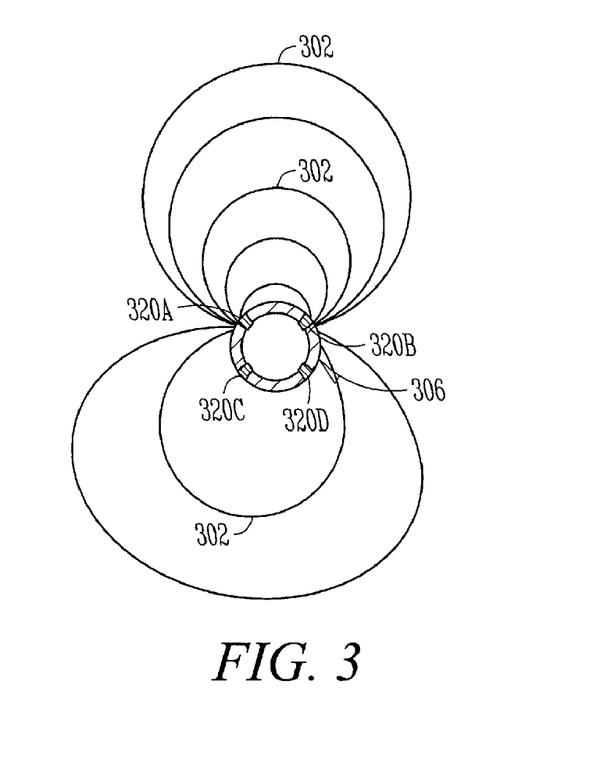
FIG. 3 illustrates, in cross-section, a current density field distribution between two electrodes, as constructed in accordance with at least one embodiment.

FIG. 3 illustrates, in cross-section, a distal portion of a neural stimulation lead 306 and a stimulation current density field 302 emerging from an intra-lead electrode vector combination including electrodes 320A and 320B. In this example, the current density field 302 takes on a circumferential shape which is selectively applied to surrounding nerve tissue for treatment of a disorder, such as a medical, psychiatric, or neurological disorder. As shown, the stimulation current density field 302 diminishes as the distance increases from the pair of activated electrodes 320A and 320B (i.e., the selected stimulation electrode vector). FIG. 3 further shows that the lead 306 includes two additional, non-activated electrodes 320C and 320D, which may also be used in a vector combination to selectively stimulation nerve tissue.

Figure 4:
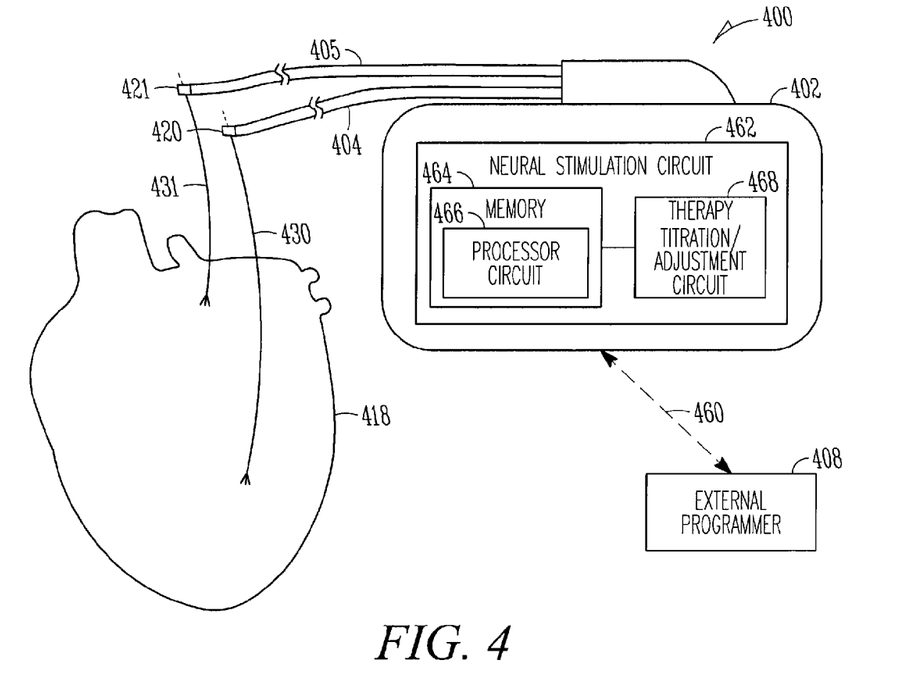
FIG. 4 illustrates a neural stimulation system including an implantable medical device, a plurality of neural stimulation leads, an external programmer, and an environment in which portions of the neural stimulation leads may be disposed, as constructed in accordance with at least one embodiment.

FIG. 4 illustrates a neural stimulation system 400 and portions of an environment in which the system 400 may be used. In this example, the neural stimulation system 400 includes an IMD 402 that delivers neural stimulation pulses through neural stimulation leads 404, 405, an external programmer 408, and a telemetry link 460 providing communication between the IMD 402 and the external programmer 408. For illustrative purposes only, FIG. 4 shows that neural stimulation lead 405 includes an electrode 421 coupled to a selected nerve target 431 of the sympathetic nervous system, and neural stimulation lead 404 includes an electrode 420 coupled to a selected nerve target 430 of the parasympathetic nervous system.

Selected nerve targets 430, 431 innervate the heart 418. In various embodiments, the IMD 402 provides neural stimulation to any one or more nerve targets through the neural stimulation leads 404, 405, and in this way, modulates autonomic balance. As discussed above, the nerve targets may be stimulated using electrodes disposed on various types of neural stimulation leads, such as neural stimulation cuff leads, neural stimulation intravascular leads, or neural stimulation subcutaneous leads. In one embodiment, a cuff electrode is used for placement around an aortic, carotid, or vagus nerve. In another embodiment, an intravascularly-placed electrode within an internal jugular vein, for example, is used to stimulate a targeted portion of the vagus nerve, or within an aorta or pulmonary artery positioned to stimulate a nerve target proximate thereto. In addition, wireless electrodes in communication with the IMD 402 may also be used for stimulation purposes.

The IMD 402 delivers the neural stimulation pulses and includes, among other things, a neural stimulation circuit 462. The illustrated neural stimulation circuit 462 includes a programmable memory 464 for storing instructions on which the IMD 402 operates, a processor circuit 466 to process sensed physiologic data or feedback, and a therapy titration/adjustment circuit 468 which receives the resulting physiologic feedback which can be representative of the efficacy of any applied therapy (e.g., stimulation pulses). In various embodiments, the IMD 402 is capable of monitoring signals indicative of a status of one or more physiologic parameters or delivering therapies in addition to the neural stimulation. Examples of such additional therapies include cardiac pacing therapy, cardioversion/defibrillation therapy, cardiac resynchronization therapy, cardiac remodeling control therapy, drug therapy, cell therapy, or gene therapy. In various embodiments, the IMD 402 delivers the neural stimulation therapy in coordination with one or more such additional therapies.

The external programmer 408 provides for control of, and communication with, the IMD 402 by a physician or other caregiver. In one embodiment, the external programmer 408 is a patient management system including an external device communicating with the IMD 402 via the telemetry link 460, a remote device in a relatively distant location (e.g., a personal digital assistant (PDA)), and a telecommunication network linking the external device and the remote device. In this way, the patient management system allows access to the IMD 402 from a remote location, such as for monitoring patient status or adjusting therapies.

As discussed, the telemetry link 460 provides communication between the IMD 402 and the external programmer 408. In one embodiment, the telemetry link 460 is an inductive telemetry link. In another embodiment, the telemetry link 460 is a far-field radio-frequency (RF) telemetry link. In various embodiments, the telemetry link 460 provides for data transmission from the IMD 402 to the external programmer 408. This includes, for example, transmitting real-time physiologic data acquired by the IMD 402, extracting physiologic data acquired by and stored in the IMD 402, extracting patient history data such as an occurrence of an arrhythmia and therapy deliveries recorded in the IMD 402, or extracting data indicating an operational status of IMD 402 (e.g., battery status or lead impedance). The telemetry link 460 also provides for data transmission from the external programmer 408 to the IMD 402. This includes, for example, programming (via a user-interface) the IMD 402 to acquire physiologic data, programming the IMD 402 to perform at least one self-diagnostic test (such as for a device operational status), or programming the IMD 402 to deliver one or more therapies or to adjust the delivery of one or more therapies.

Figure 5:
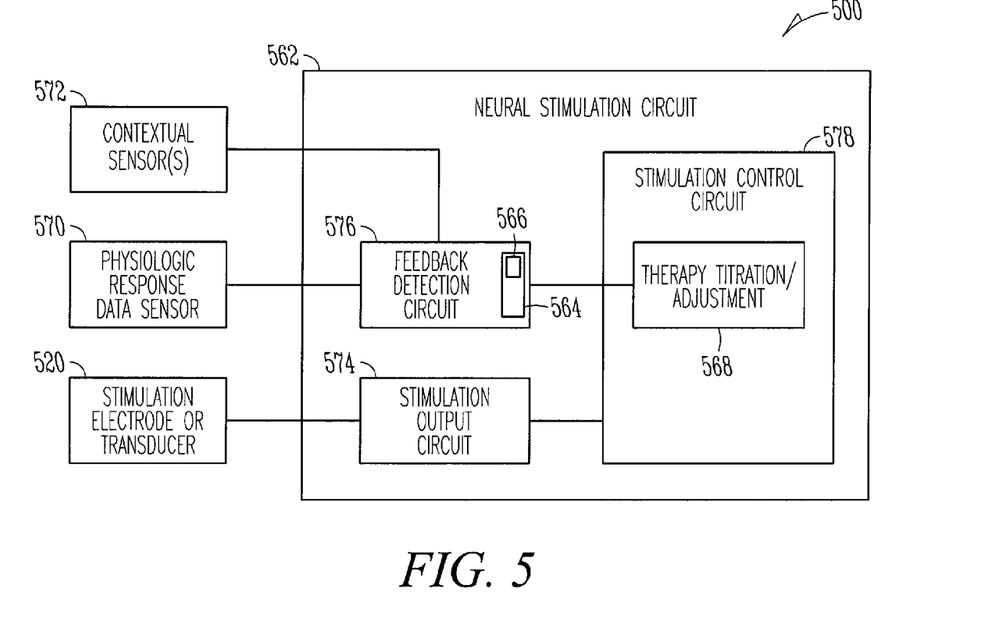
FIG. 5 illustrates a block diagram of portions of a neural stimulation system, as constructed in accordance with at least one embodiment.

FIG. 5 illustrates a block diagram of at least one embodiment of portions of a neural stimulation system 500. The neural stimulation system 500 of this embodiment includes a physiologic response data sensor 570 adapted to sense one or more physiologic responses to any applied neural stimulation, a contextual sensor 572 adapted to sense a pre-stimulation status of one or more physiologic parameters (e.g., a change in heart rate or blood pressure) or otherwise provide a more complete picture of a patient's physiology, a stimulation electrode/transducer 520, and a neural stimulation circuit 562.

The neural stimulation circuit 562 includes a stimulation output circuit 574, a feedback detection circuit 576, and a stimulation control circuit 578. The stimulation control circuit 578 controls the delivery of the neural stimulation pulses and includes a therapy titration/adjustment circuit 568. The stimulation output circuit 574 delivers neural stimulation pulses upon receiving a pulse delivery signal from the stimulation control circuit 578. The pulse delivery signal is generated, at least in part, by data analysis performed by a processor circuit 566, such as the comparison of one or more pre-stimulation physiologic parameters collected by the contextual sensor 572 and physiologic threshold parameter valves stored in a programmable memory 564. The physiologic response data sensor 570 provides signals indicative of the responses of one or more physiologic parameters to the applied neural stimulation. The feedback detection circuit 576 receives the signal indicative of the responses and processes the signals to provide a neural stimulation feedback signal.

Many types of physiologic responses may be gathered by the physiologic response data sensor 570 and processed by the feedback detection circuit 576. In various embodiments, the responses include cardiac activity, such as heart rate, HRV, HRT, PR interval, T-wave velocity, or action potential duration. In various embodiments, the responses include non-cardiac responses, such as respiration or blood pressure. In various embodiments, the responses include QT intervals or atrial/ventricular refractory periods. The therapy titration/adjustment circuit 568 uses the stimulation feedback signal to titrate the therapy generated by the stimulation output circuit 574 to provide the desired physiologic response (e.g., modulate the cardiac response or non-cardiac response). The feedback detection circuit 576 can provide the neural stimulation feedback signal based on the physiologic response data sensor 570 or the contextual sensor 572. Besides sensing one or more pre-stimulation physiologic parameters, the contextual sensor(s) 572 may further be used to avoid incomplete data from affecting the neural stimulation therapy applied to a selected nerve target. Examples of such contextual sensors 572 include an activity sensor, a posture sensor, or a timer. Any one or combination of two or more contextual inputs can be used by the feedback detection circuit 576. For example, an elevated heart rate may be representative of exercise rather than a reason for titrating the neural stimulation therapy.

The stimulation electrode/transducer 520 is what ultimately delivers the neural stimulation therapy to the selected nerve target. The polarity and location of the electrodes chosen to deliver the stimulation current and the parameters of the stimulation current (e.g., amplitude, frequency, burst frequency, duty cycle, or pulse width, etc.) may be based on a status of the one or more sensed physiologic responses, a desire for low stimulation thresholds, the particular disorder the stimulation is meant to treat, or a desire to minimize or abate stimulation side-effects. As one example, the neural stimulation circuit 562 in conjunction with the physiologic response data sensor 570 may monitor autonomic balance through frequency response analysis of a monitored PR interval, and the stimulation cathode and anode locations may be adjusted to maximize parasympathetic activation.

Advantageously, the present subject matter allows for a physician or other caregiver (via an external user-interface) or an IMD itself to choose among numerous electrode vector combinations for stimulating a selected nerve target within a nerve trunk. The numerous electrode vector combinations allow the physician or the IMD to recurrently selected one or more electrode combinations which optimize or provide an acceptable balance of one or a combination of physiologic feedback responses, a minimal degree of stimulation side-effects, or a low stimulation threshold parameter, among other things.

Figure 6:
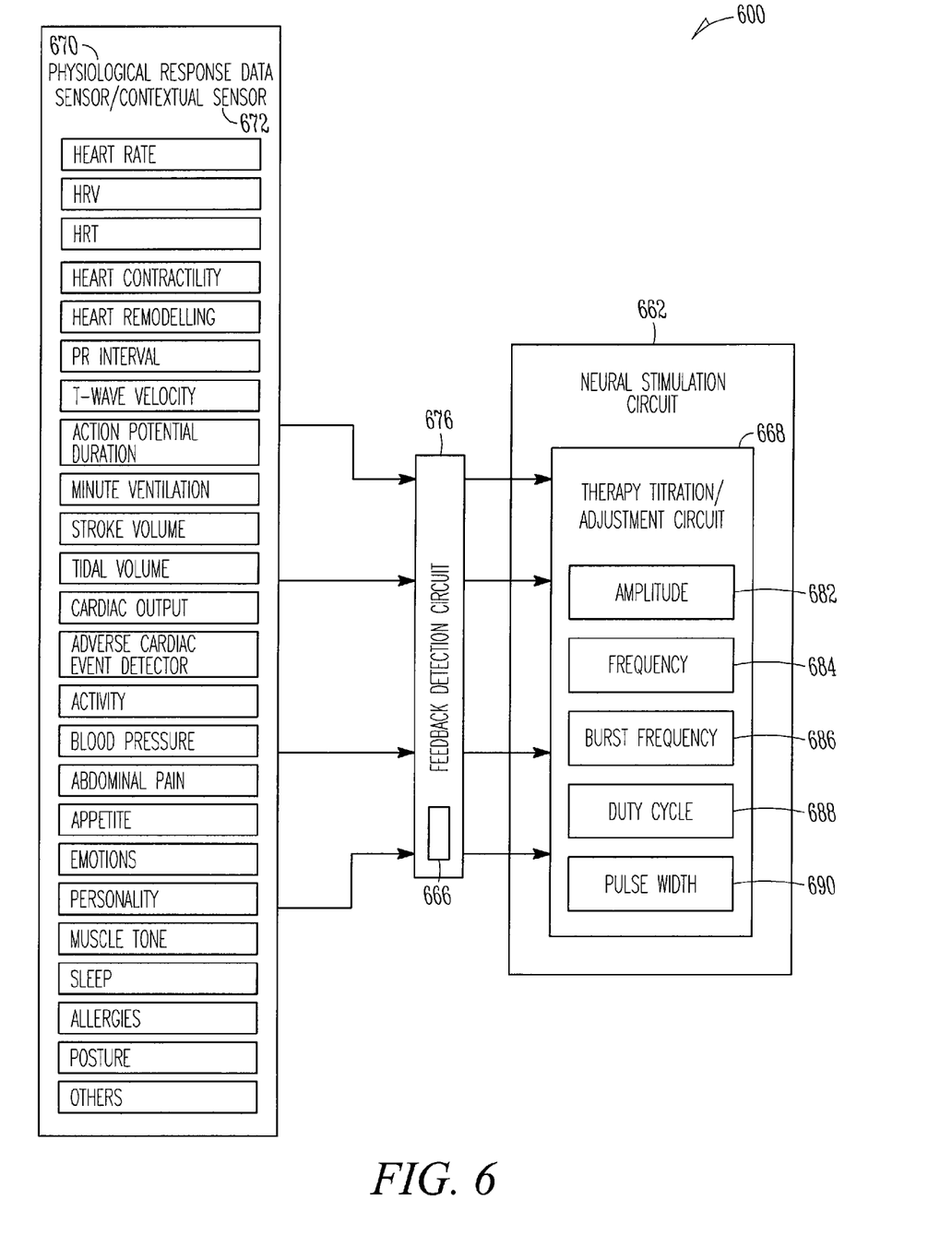
FIG. 6 illustrates portions of a neural stimulation system and various physiologic parameters that can be monitored or received by the system to provide an indication of a change in autonomic balance or stimulation feedback, as constructed in accordance with at least one embodiment.

FIG. 6 illustrates portions of a neural stimulation system 600 and various physiologic parameters which may be used in the selection of the optimal or acceptable electrode vector combination and signal parameters for stimulating a selected target nerve. Various embodiments of the system 600 include any one or combination of a physiologic response data sensor 670 or a contextual sensor 672, which are capable of directing the therapy titration/adjustment circuit 668 of the neural stimulation circuit 662 to appropriately apply a needed or desired level of neural stimulation to an optimal electrode vector. According to various embodiments, the system 600 includes means to modulate autonomic balance based one or more of the following sensed physiologic parameters: heart rate, HRV, HRT, heart contractility, heart remodeling, PR interval, T-wave velocity, action potential duration, minute ventilation, stroke volume, tidal volume, cardiac output, adverse cardiac event detector, activity, blood pressure, abdominal pain, appetite, emotions, personality, muscle tone, sleep, allergies, or posture.

A feedback detection circuit 676 receives a signal indicative of the sensed physiologic parameters and processes the signal to provide a signal which may be used, at least in part, by the neural stimulation circuit 662 to generate an appropriate pulse delivery signal. In various embodiments, a processor 666 of the feedback detection circuit 676 determines whether the sensed physiologic parameters are within an acceptable range. For instance, if the processor 666 determines a sensed heart rate exceeds a certain target range, the processor 666 may send appropriate instructions to the neural stimulation circuit 662, and more specifically to the therapy titration/adjustment circuit 668, for use in generating the pulse delivery signal.

According to various embodiments, the therapy titration/adjustment circuit 668 includes any one of the following modules: a module 682 to change the amplitude of the stimulation pulse; a module 684 to change the frequency of the stimulation pulse; a module 686 to change the burst frequency of the stimulation pulse; a module 688 to change the duty cycle of the stimulation pulse; or a module 690 to change the pulse width of the stimulation pulse. According to some embodiments, the neural stimulation circuit 662 is adapted to set or adjust any one or any combination of stimulation features. Examples of stimulation features include the amplitude, frequency, polarity and wave morphology of the stimulation signal. Examples of wave morphology include a square wave, triangle wave, sinusoidal wave, and waves with desired harmonic components to mimic white noise such as is indicative of naturally-occurring baroreflex stimulation. Some embodiments of the neural stimulation circuitry are adapted to generate a stimulation signal with a predetermined amplitude, morphology, pulse width and polarity, and are further adapted to respond to a control signal to modify at least one of the amplitude, wave morphology, pulse width and polarity. Some embodiments of the neural stimulation circuitry are adapted to generate a stimulation signal with a predetermined frequency, and are further adapted to respond to a control signal from the controller to modify the frequency of the stimulation signal.

Figure 7:
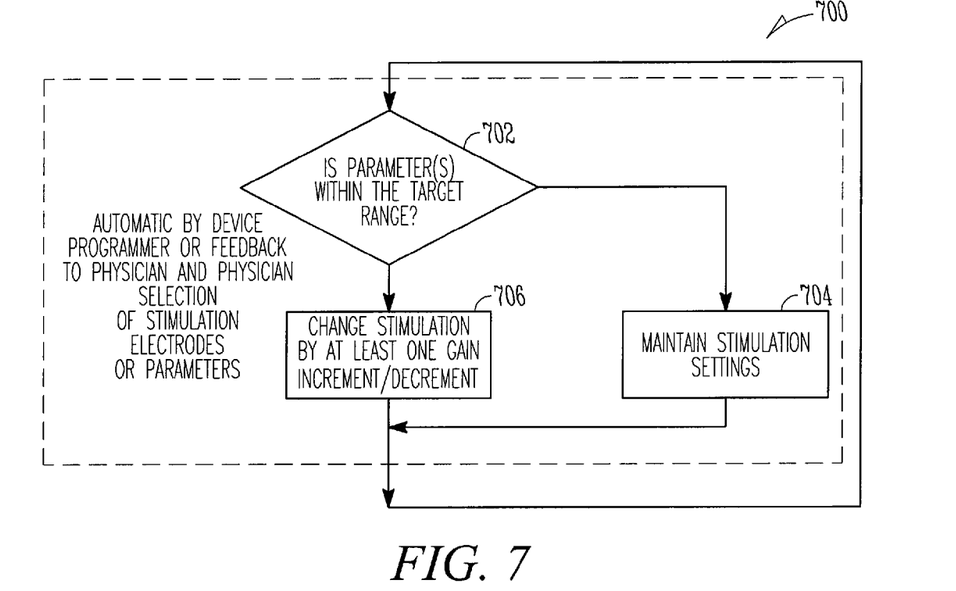
FIG. 7 illustrates a method of processing sensed signals indicative of a status of one or more physiologic parameters to determine what one or more neural stimulation parameters, if any, need to be applied for modulation of autonomic balance, as constructed in accordance with at least one embodiment.

FIG. 7 illustrates an embodiment of a method 700 to determine one or more neural stimulation parameters using one or more sensed physiologic parameters. The method 700 may be performed automatically by device or via feedback to a physician or other caregiver and physician selection of the stimulation parameters. At 702, a determination is made as to whether the one or more sensed physiologic parameters are within a specified target range. If the one or more sensed parameters are determined to be within the target range, the stimulation settings are maintained 704, and the process returns to 702. If the one or more sensed parameters are determined to be outside of the target range, the process proceeds to 706 to titrate the neural stimulation by at least one gain increment or decrement, depending on the selected electrode vector combination used, to move the sensed parameters toward the target range. Various examples provide other ranges above, below, or within (i.e., a sub-range within) the target range. Various stimulation adjustment protocols (e.g., gain) can be used depending on the range, sub-range, etc. For example, large adjustments may be made by adjusting one stimulation parameter (e.g., frequency) and smaller adjustments can be made by adjusting another stimulation parameter (e.g., amplitude).

Various embodiments titrate the neural stimulation by increasing the intensity of the stimulation or decreasing the intensity of the stimulation. Various embodiments titrate the stimulation by changing a feature of the signal (e.g., amplitude, frequency, pulse duration or waveform). Various embodiments titrate the stimulation by changing a stimulation electrode vector which changes the neural stimulation. Some embodiments change the electrode vector to change between stimulating neural traffic and inhibiting neural traffic. Various embodiments titrate the stimulation by changing the electrodes used to provide the electrical therapy. Thus, given N electrodes, the stimulation can change from using a first set of electrodes selected from the N electrodes to a second set of electrodes selected from the N electrodes. An electrode can be in one set but not the other, or can be in both sets. Some sets only include electrodes that are not in the other set.

Figure 8:
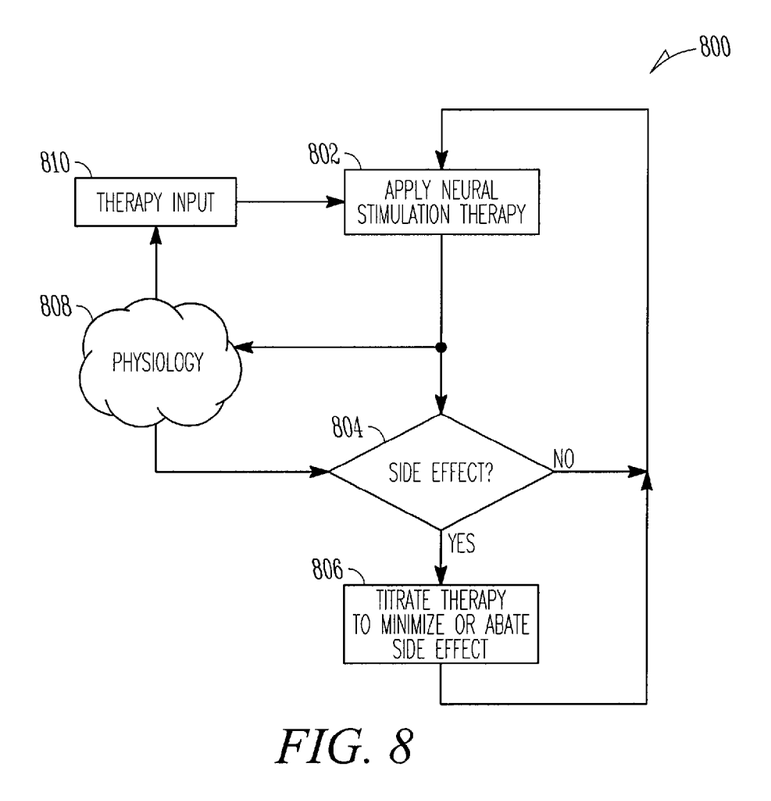
FIG. 8 illustrates a method to minimize or abate stimulation side-effects, as constructed in accordance with at least one embodiment.

FIG. 8 illustrates a method 800 to minimize or abate stimulation side-effects when neural stimulation is applied. A neural stimulation therapy is applied at 802. According to various embodiments, the neural stimulation is turned ON and OFF based on a therapy schedule, and includes a train of pulses when the stimulation is turned ON. At 804, it is determined whether an adverse side-effect attributable to the neural stimulation is detected. Examples of common adverse side-effects include coughing, voice related side-effects such as voice alterations or laryngismus, respiratory related side-effects such as dyspnea or apnea, cardiac related side-effects such as bradycardia, tachyarrhythmias, or reduced cardiac output, and patient discomfort such as nausea, inflammation of throat, abnormal sensations, or upset stomach. Various sensors can be used to detect the adverse side-effect(s). As one example, an impedance sensor, an accelerometer, or an acoustic sensor can be used to detect coughing. An acoustic sensor can also be used to detect voice-related side effects. As another example, a respiratory sensor, such as minute ventilation and transthoracic impedance, can be used to detect respiratory related side-effects. As yet another example, cardiac related side-effects can be detected using a heart rate sensor, an arrhythmia detector, a blood pressure sensor, or a blood flow sensor. As a further example, patient discomfort can be determined by one or more inputs from a patient or physician.

In various embodiments, for example, it is determined whether the neural stimulation and side-effects occur at or near the same time to determine that the neural stimulation caused the side-effect. If a side-effect is not detected, the process returns to 802 to continue to apply the neural stimulation therapy. If a side-effect is detected, the process proceeds to 806, where the intensity of the neural stimulation therapy is titrated to minimize or abate the side-effect. For example, upon detection of the side effect, the intensity of neural stimulation is automatically adjusted below the side-effect threshold or to different electrodes while maintaining stimulation at a therapeutic level. The stimulation intensity can be adjusted by changing stimulation electrodes or by adjusting the amplitude, frequency, duty cycle, or pulse width of the neural stimulation signal. The side-effect threshold may increase over time, and the intensity of the neural stimulation therapy can increase with it while remaining below the side-effect threshold.

Neural stimulation affects physiology 808 through a neural network. Therapy inputs 810 can be sensed or derived using physiology sensors, which can provide a feedback signal used to control the applied neural stimulation therapy. Physiology sensors or other inputs can be used to sense, determine or otherwise derive that a side-effect is occurring, as illustrated at 804. For example, an embodiment includes a cough sensor adapted to determine when a cough is attributable to applied neural stimulation. Other embodiments use patient or physician input for use in determining when a patient is experiencing a side-effect attributable to the neural stimulation.

Figure 9:
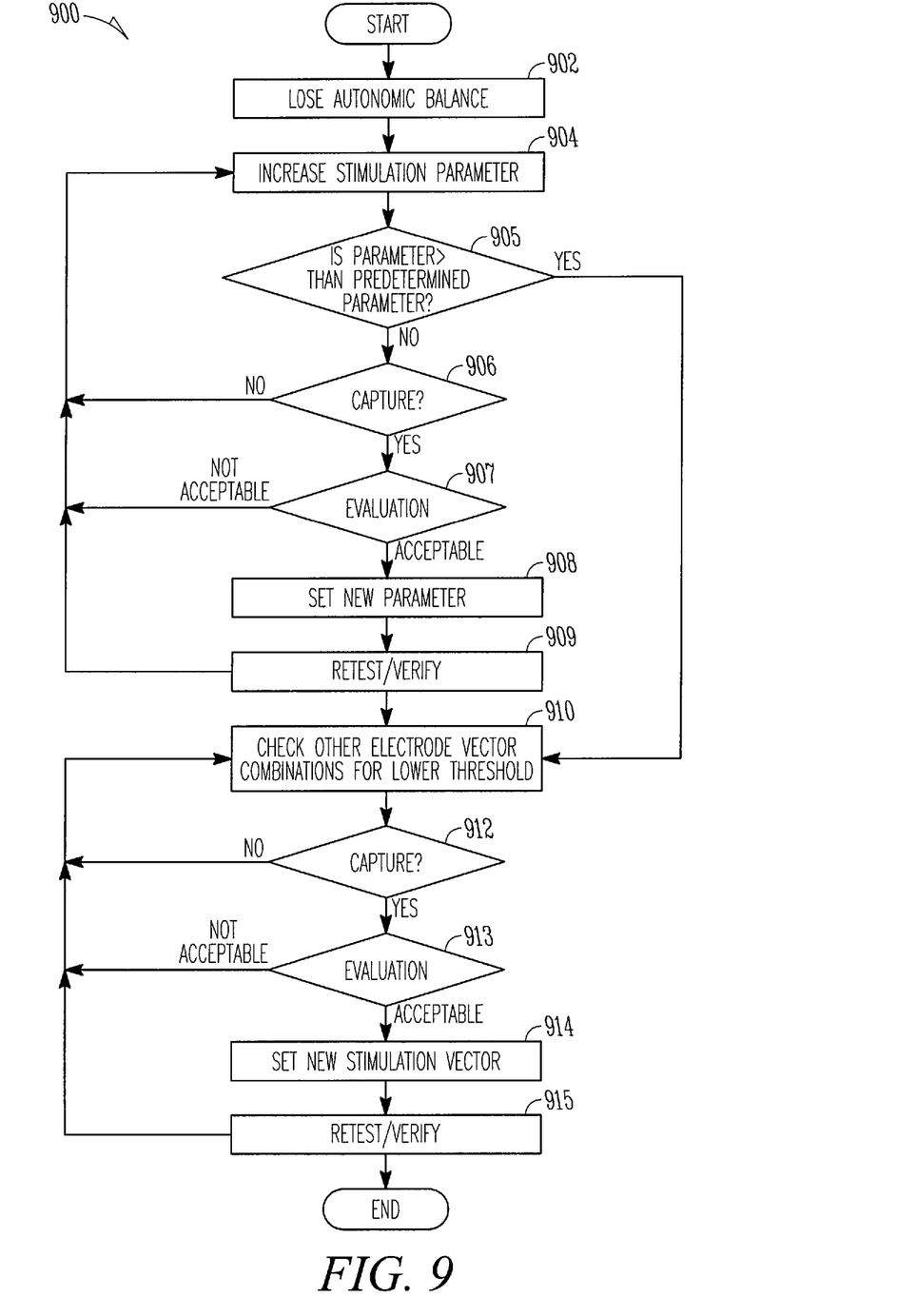
FIG. 9 illustrates a method to regain autonomic balance after it is lost using a stimulation electrode vector combination having a low neural stimulation threshold, as constructed in accordance with at least one embodiment.

FIG. 9 illustrates a method 900 to regain autonomic balance after it is lost via a low neural stimulation threshold. At 902, it is determined whether or not autonomic balance is lost. If autonomic balance is lost, a stimulation parameter (e.g., current amplitude) is increased at 904. At 905, the increased parameter is compared with a predetermined parameter threshold. If the increased stimulation parameter is greater than (or in some case, substantially equal to) the predetermined parameter threshold, a new set of electrodes are checked for a lower parameter threshold at 910.

If the increased stimulation parameter is less than the predetermined parameter threshold, a determination of whether autonomic balance has been regained is made at 906. If balance is not regained, the process returns to 904 where the stimulation parameter is increased again. If balance is regained, at 907, the new stimulation parameter is evaluated at 907. If the evaluation is deemed acceptable, at 908, the new stimulation voltage is set. If the evaluation is deemed non-acceptable, the process returns to 904. At 909, the new stimulation voltage is retested/verified to ensure that it results in autonomic balance. If balance is not regained by the new stimulation voltage, the process returns to 904 where the stimulation voltage is increased again.

At 912, a determination of whether autonomic balance is regained by the new set of electrodes is made. If balance is regained by the new set of electrodes, at 913, the new stimulation electrode vector is evaluated. If the evaluation is deemed acceptable, at 914, the new stimulation electrode vector is set. If the evaluation is deemed non-acceptable, the process returns to 910. At 915, the new stimulation parameter is retested/verified to ensure that it results in autonomic balance. If balance is not regained by the new stimulation parameter, a second new set of electrodes are checked for lower voltage thresholds at 910.

As discussed, the present neural stimulation systems and methods can effectively and efficiently be used to treat and control a variety of medical, psychiatric, or neurological disorders by modulation of autonomic balance. The autonomic balance is modulated by steering a (therapeutic) stimulation current density through a selected nerve target via an optimal or acceptable stimulation electrode vector. Because the system includes a multiplicity of electrodes in an electrode array around a nerve, the system has many options to chosen from to determine the optimal or acceptable stimulation electrode vector. In some examples, the electrode vector used to steer the therapeutic current is that vector which maintains the best combination of low stimulation thresholds, results in reduce adverse side-effects, and results in acceptable physiologic feedback.

It is to be understood that the above Detailed Description is intended to be illustrative, and not restrictive. For instance, any of the aforementioned examples may be used individually or with any of the other examples. Many other examples may be apparent to those of skill in the art upon reviewing the above description. Therefore, the scope of the present systems and methods should be determined with reference to the appended claims, along with the full scope of legal equivalents to which such claims are entitled. In the appended claims, the terms "including" and "in which" are used as the plain-English equivalents of the respective terms "comprising" and "wherein." Also, in the following claims, the terms "including" and "comprising" are open-ended, that is, a system, assembly, article, or process that includes elements in addition to those listed after such a term in a claim are still deemed to fall within the scope of such claim.

The Abstract of the Disclosure is provided to comply with 37 C.F.R. §1.72(b), requiring an abstract that will allow the reader to quickly ascertain the nature of the technical disclosure. It is submitted with the understanding that it will not be used to interpret or limit the scope or meaning of the claims.

What is claimed is:

1. A system for stimulating a selected nerve target, the system comprising:
   two or more neural stimulation leads;
   an array of electrodes disposed, at least in part, on the two or more neural stimulation leads and adapted to be implantably positioned adjacent a single peripheral nerve trunk, the array of electrodes including at least a first electrode disposed on a first neural stimulation lead and a second electrode disposed on a second neural stimulation lead;
   an implantable medical device including a programmable memory adapted to receive a programming signal, at least partially based on a physiologic signal generated by a physiologic sensor and indicative of a status of one or more physiologic parameters, for selectively applying electrical stimulation to a stimulation electrode vector combination of at least two electrodes within the electrode array; and
   wherein the two or more neural stimulation leads include or are attached to a positioning feature configured for allowing the leads to be implantably positioned adjacent to the single peripheral nerve trunk.

2. The system of claim 1, further comprising one or more lead positioning members adapted to connect to and maintain a desired geometric relationship between portions of the two or more neural stimulation leads near the single peripheral nerve trunk;
   wherein the one or more lead positioning members extend in a direction different than a lead axis at the point of connection.

3. The system of claim 2, wherein the one or more lead positioning members are adapted to position the two or more neural stimulation leads adjacent the single peripheral nerve trunk, and include at least one electrode thereon.

4. The system of claim 1, further comprising an external programmer adapted to receive and communicate one or more remotely generated inputs to the implantable medical device.

5. The system of claim 1, further comprising a cardiac stimulation lead including at least one electrode thereon, the cardiac stimulation lead adapted to be implantably positioned within, on, or about a heart and in electrical contact with the implantable device.

6. The system of claim 1, wherein the implantable medical device is programmable to cause the electrodes to assume positive or negative polarity.

7. The system of claim 1, wherein the two or more neural stimulation leads include one or more of a neural stimulation cuff lead, a neural stimulation intravascular lead, or a neural stimulation subcutaneous lead.

8. The system of claim 1, wherein the one or more physiologic parameters include at least one of a heart rate parameter, a heart rate variability parameter, a PR interval parameter, a T-wave velocity parameter, or an action potential duration parameter.

9. The system of claim 1, wherein the one or more physiologic parameters include at least one of a heart contractility parameter, a heart remodeling parameter, a stroke volume parameter, a cardiac output parameter, or a blood pressure parameter.

10. The system of claim 1, wherein the one or more physiologic parameters include at least one of a minute ventilation parameter or a tidal volume parameter.

11. The system of claim 1, wherein the one or more physiologic parameters include at least one of an adverse cardiac event parameter, an activity parameter, an abdominal pain parameter, an appetite parameter, an emotions parameter, a personality parameter, a muscle tone parameter, a sleep parameter, an allergy parameter, or a posture parameter.

12. The system of claim 1, comprising one or more physiologic sensors adapted to generate a physiologic signal indicative of a status of one or more physiologic parameters.

13. A system for stimulating a nerve target, the system comprising:
  two or more neural stimulation leads;
  an array of electrodes disposed, at least in part, on the two or more neural stimulation leads and adapted to be implantably positioned adjacent a single peripheral nerve target, the array of electrodes including at least a first electrode disposed on a first neural stimulation lead and a second electrode disposed on a second neural stimulation lead;
  and
  an implantable medical device including,
    a programmable memory adapted to receive a programming signal, which is at least partially based on a physiologic signal generated by a physiologic sensor and indicative of a status of one or more physiologic parameters, for selectively applying electrical stimulation to a stimulation electrode vector combination of at least two electrodes within the electrode array, and
    a means for titrating one or more parameters of the applied electrical stimulation;
  wherein the two or more neural stimulation leads include a bias portion, a cuff, a transvascular size and shape, or attach to a lead position member to maintain a desired geometric relationship relative to one another near the single peripheral nerve target.

14. The system of claim 13, further comprising means for choosing the at least two electrodes of the electrode array used in the selective application of electrical stimulation.

15. The system of claim 12, wherein the one or more physiologic sensors include a cough sensor, and wherein the implantable medical device is adapted to receive a cough status indicative signal from the cough sensor and determine whether a detected cough is attributable to the applied electrical stimulation and automatically titrate the electrical stimulation to reduce or abate the cough.

16. A method of stimulating a nerve target, the method comprising:
  disposing a portion of two or more neural stimulation leads carrying an array of electrodes adjacent a single peripheral nerve target, the array of electrodes including at least a first electrode disposed on a first neural stimulation lead and a second electrode disposed on a second neural stimulation lead;
  selectively employing a stimulation electrode vector combination of at least two of the electrodes within the array to direct electrical stimulation applied to the electrodes to the nerve target;
  delivering electrical stimulation to the selectively employed electrodes; and
  modulating autonomic balance.

17. The method of claim 16, further comprising evaluating a plurality of electrode vector combinations for an ability to sense or stimulate the single peripheral nerve target.

18. The method of claim 16, further comprising detecting a physiologic response to the electrical stimulation.

19. The method of claim 18, wherein detecting the physiologic response to the electrical stimulation includes detecting a non-cardiac response to the electrical stimulation.

20. The method of claim 18, wherein detecting the physiologic response to the electrical stimulation includes detecting a cardiac response to the electrical stimulation.

21. The method of claim 18, further comprising titrating the electrical stimulation using the detected physiologic response.

22. The method of claim 21, wherein titrating the electrical stimulation includes titrating one or more of an amplitude, a frequency, a burst frequency, a duty cycle, or a pulse width of an electrical stimulation signal.

23. The method of claim 18, further comprising employing at least one electrode within the array other than the at least two electrodes initially used to direct the electrical stimulation to the single peripheral nerve target.

24. The method of claim 16, comprising maintaining the desired geometric relationship between the two or more neural stimulation leads near the single peripheral nerve target, including connecting the leads via one or more lead positioning members;
  wherein the one or more lead positioning members extend in a direction different than a lead axis at the point of connection.

25. The method of claim 16, wherein disposing the two or more neural stimulation leads adjacent the single peripheral nerve target includes disposing at least one neural stimulation lead carrying an electrode in a venous or arterial vessel adjacent the single peripheral nerve target.

26. The method of claim 16, wherein disposing the two or more neural stimulation leads adjacent the single peripheral nerve target includes disposing at least one neural stimulation lead using a surgical dissection procedure, an endoscopy procedure, or a transvascular procedure.

27. The method of claim 16, wherein disposing the two or more neural stimulation leads adjacent the single peripheral nerve target includes disposing the two or more leads adjacent a single vagus nerve.

28. The method of claim 16, wherein delivering the electrical stimulation to the selectively employed electrodes includes delivering an electrical stimulation signal and minimizing stimulation side-effects.

* * * * *